United States Patent [19]

Miller et al.

[11] Patent Number: 5,109,027
[45] Date of Patent: Apr. 28, 1992

[54] CATALYTIC PROCESS FOR PRODUCING OLEFINS OR HIGHER ALCOHOLS FROM SYNTHESIS GAS

[75] Inventors: Jeffrey T. Miller, Naperville; Cecelia A. Radlowski, Riverside, both of Ill.

[73] Assignee: Amoco Corporation, Chicago, Ill.

[21] Appl. No.: 702,137

[22] Filed: May 13, 1991

Related U.S. Application Data

[63] Continuation-in-part of Ser. No. 365,915, Jun. 14, 1989, abandoned, which is a continuation-in-part of Ser. No. 365,529, Jun. 13, 1989, abandoned.

[51] Int. Cl.$^5$ ............................ C07L 1/04; C07C 27/06
[52] U.S. Cl. ....................................................... 518/717
[58] Field of Search .......................................... 518/717

[56] References Cited

U.S. PATENT DOCUMENTS

| | | | |
|---|---|---|---|
| 1,963,119 | 6/1930 | Dreyfus | 260/156 |
| 2,850,515 | 9/1958 | Riblett et al. | 260/449.6 |
| 4,122,110 | 10/1978 | Sugier et al. | 260/449.5 |
| 4,423,156 | 12/1983 | Büssemeier et al. | 518/717 |
| 4,440,663 | 4/1984 | Chang et al. | 502/331 |
| 4,542,117 | 9/1985 | Morris et al. | 502/66 |
| 4,542,122 | 9/1985 | Payne et al. | 502/325 |
| 4,559,316 | 12/1985 | Mazanec et al. | 502/73 |
| 4,564,642 | 1/1986 | Büssemeier et al. | 518/717 |
| 4,564,643 | 1/1986 | Shibata et al. | 518/717 |
| 4,576,968 | 3/1986 | Nay et al. | 518/713 |
| 4,584,323 | 4/1986 | Soled et al. | 518/700 |
| 4,585,798 | 4/1986 | Beuther et al. | 518/715 |
| 4,585,799 | 4/1986 | Morris et al. | 518/717 |
| 4,640,766 | 2/1987 | Post et al. | 208/111 |
| 4,657,885 | 4/1987 | Fiato et al. | 502/241 |
| 4,659,742 | 4/1987 | Courty et al. | 518/700 |
| 4,663,305 | 5/1987 | Mauldin et al. | 502/304 |
| 4,751,248 | 6/1988 | Lin et al. | 518/707 |
| 4,826,800 | 5/1989 | McAteer | 502/303 |
| 4,880,763 | 11/1989 | Eri et al. | 502/302 |

FOREIGN PATENT DOCUMENTS

| | | |
|---|---|---|
| 1512743 | 6/1978 | United Kingdom . |
| 1553361 | 9/1979 | United Kingdom . |
| 2047249 | 11/1980 | United Kingdom . |
| 2118061 | 10/1983 | United Kingdom . |

OTHER PUBLICATIONS

Courty et al., "The I.F.P. Process for Production of $C_1$-$C_6$ Alcohols from Synthesis Gas" in *Petrochemical Raw Materials* (undated), pp. 173-179.
Courty et al., "$C_1$-$C_6$ Alcohols from Syngas" in *Hydrocarbon Processing*, Nov. 1964, pp. 105-108.
Courty et al., "$C_1$-$C_6$ Alcohols From Synthesis Gas on Copper-Cobalt Catalysts", *Journal of Molecular Catalysis*, 17 (1982), pp. 241-254.
"IFP Details Synthesis Gas to Higher Alcohols Process" in *European Chemical News*, Sep. 12, 1983.
Fujimoto et al., "Synthesis of $C_1$-$C_7$ Alcohols from Synthesis Gas With Supported Cobalt Catalysts", *Applied Catalysis*, 13 (1985), pp. 289-293.
*Catalysis* (Emmett, Ed.), vol. V, pp. 151-152.

*Primary Examiner*—Howard T. Mars
*Attorney, Agent, or Firm*—Nick C. Kottis; William H. Magidson; Ralph C. Medhurst

[57] ABSTRACT

A process for converting synthesis gas to olefins or higher alcohols depending on operating pressure includes an alkali metal-containing cobalt synthesis gas conversion catalyst. The process allows great flexibility in selecting the product mix by changing process conditions.

29 Claims, No Drawings

CATALYTIC PROCESS FOR PRODUCING OLEFINS OR HIGHER ALCOHOLS FROM SYNTHESIS GAS

CROSS-REFERENCE TO RELATED APPLICATIONS

This is a continuation-in-part of copending, commonly owned application Ser. No. 07/365,915 filed June 14, 1989, now abandoned, which in turn is a continuation-in-part of copending, commonly owned application Ser. No. 07/365,529 filed June 13, 1989, now abandoned, the disclosure of which is incorporated herein by reference.

BACKGROUND OF THE INVENTION

1. Field of the Invention

This invention relates generally to synthesis gas conversion and, more specifically, this invention relates to processes for selectively converting synthesis gas to olefins or higher alcohols.

2. Brief Description of Related Technology

Large reserves of natural gas or methane are located in remote areas of the world. As oil reserves are depleted, there is great incentive to convert this gas into a commodity liquid fuel. A number of direct methane conversion technologies, such as pyrolysis, oxidative coupling, and direct oxidation exist, but are in the early stages of development. However, there are well-established technologies for the conversion of natural gas into synthesis gas, i.e., a mixture of CO and free hydrogen.

The Fischer-Tropsch process is a well-known synthesis gas reaction for making hydrocarbons. The economics of the Fischer-Tropsch process have been investigated periodically and have generally been found to be unfavorable. The direct synthesis of higher alcohols (i.e., those having 2 or more carbon atoms per molecule) from carbon monoxide and hydrogen has attracted attention because the products are suitable as gasoline extenders and high-octane blending components.

The formation of aliphatic alcohols by the hydrogenation of carbon monoxide is represented by the following equations:

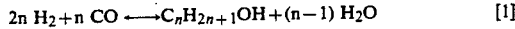

$$2n\, H_2 + n\, CO \longrightarrow C_nH_{2n+1}OH + (n-1)\, H_2O \quad [1]$$

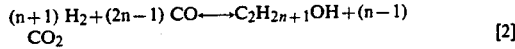

$$(n+1)\, H_2 + (2n-1)\, CO \longrightarrow C_2H_{2n+1}OH + (n-1)\, CO_2 \quad [2]$$

The hydrogenation of carbon monoxide to hydrocarbons is thermodynamically more favorable than hydrogenation to alcohols; thus, alcohol formation requires selective catalysts in order to minimize hydrocarbon formation.

Catalysts for higher alcohol processes which have reached the commercialization stage or have undergone large-scale pilot plant trials fall into three main categories. They include low temperature methanol synthesis catalysts modified with alkali metals, high temperature methanol synthesis catalysts modified with alkali metals, and modified Fischer-Tropsch catalysts.

Low temperature methanol synthesis catalysts which have been modified for higher alcohol synthesis by the addition of alkali metals usually contain both copper and zinc and may contain oxides of chromium or aluminum. The product of one such catalyst typically contains 50–70 percent methanol depending upon the $H_2/CO$ ratio of the synthesis gas feed, the balance being $C_2$–$C_8$ alcohols and partially hydrogenated oxygenates. The water content can be reduced to a few percent, while the content of light hydrocarbons is negligible. Typical reaction conditions are 1500 psig and 520° F. The main shortcomings of this type of higher alcohol catalyst include the presence of a high fraction of methanol in the product, sensitivity of the catalyst to the carbon dioxide level, increased light hydrocarbon production, and deterioration of catalyst activity with time, especially when operated at higher temperatures.

High temperature methanol synthesis catalysts which have been modified with alkali metals to produce higher alcohols usually contain ZnO and $Cr_2O_3$ and may also contain oxides of copper. Typical processes of this type operate at $H_2/CO$ ratios of 0.5–3, a temperature of 625°–800° F., a pressure of 1300–2600 psig, and a gas hourly space velocity (GHSV) of 3000–15,000/hr. The alcohol product is about 70 percent methanol, with the remainder being $C_2$–$C_5$+ higher alcohols and oxygenates. Isobutanol is the principal higher alcohol. At these conditions water can be about 20 percent of the crude product, and hydrocarbon contents are low. The catalysts are quite stable with time. Main drawbacks include the presence of a large amount of methanol in the product, the need to remove large amounts of water, the need to use a synthesis gas feed with a low $H_2/CO$ ratio, and a high operating pressure.

One example of a modified Fischer-Tropsch catalyst contains $MoS_2$, CoS, and $K_2O$. This catalyst has been reported to yield about 85 percent mixed alcohols, with the remainder as $C_1$–$C_5$ paraffins.

The crude mixed alcohol product of this type of catalyst contains about 50 percent methanol, with the remainder $C_2+$ alcohols and oxygenates. Ethanol is the major higher alcohol. This catalyst effects a water-gas shift reaction at alcohol synthesis conditions and thus provides a product with less than about 3 percent water. One drawback to this process can be a high yield of light hydrocarbons. The catalyst is believed to require 25–50 ppm $H_2S$ in the feed gas to maintain acceptable activity.

The preparation of alcohols from carbon monoxide and hydrogen yields a range of alcohol chain lengths as well as linear or branched alcohols. Generally, higher alcohols which form over copper-containing catalysts are branched; those formed over Group VIII metals are predominately straight chained.

Mixed copper-cobalt alkalized catalysts have been developed by Institut Francais du Petrole for conversion of synthesis gas to higher alcohols. These catalysts generally also contain aluminum, chromium, and zinc. Although these catalysts contain both copper (a component of many methanol synthesis catalysts) and cobalt (a typical Fischer-Tropsch catalyst component), the product distribution is similar to that obtained from a modified Fischer-Tropsch catalyst, i.e., ethanol is the major $C_2+$ alcohol. A typical such catalyst would yield, on a $CO_2$-free basis, 70–80 percent oxygenates and 20–30 percent hydrocarbons. Of the oxygenates, methanol can be 50–70 percent, ethanol 16–25 percent, and the balance other alcohols and partially hydrogenated oxygenates. Such catalysts typically operate at 500 to 600° F., 1000–1500 psig, a GHSV of 3000–6000/hr, a $H_2/CO$ ratio of 2 or less, and $CO_2$ content in the feed gas of less than 3 percent. Drawbacks include the high methanol fraction in the alcohol product and the large amount of light hydrocarbons that are also produced. The performance of this type of copper-cobalt catalyst is especially sensitive to the method by which it is prepared. Large-scale industrial preparation may require very tight controls to ensure an active material.

SUMMARY OF THE INVENTION

It is an object of the invention to overcome one or more of the problems described above.

According to the invention, a process for converting synthesis gas to olefins or to alcohols having at least 2 carbon atoms per molecule is provided wherein synthesis gas is contacted with a substantially copper-free, alkali metal- and cobalt-containing synthesis gas conversion catalyst to produce an effluent product containing unconverted synthesis gas, water, and a substantial proportion of olefins or alcohols having at least 2 carbon atoms per molecule. The catalyst preferably contains oxidized zinc, with a low zinc to cobalt ratio.

The inventive process provides a product which is relatively rich in olefins or higher alcohols depending on the operating pressure. When the process is operated at high reaction pressures to produce alcohols, the product is relatively lean in methanol. When the process is operated at low reaction pressures, the product is rich in olefins, especially $C_2$-$C_6$ olefins, with relatively few paraffin or oxygenated products.

Other objects and advantages of the invention will be apparent to those skilled in the art from a review of the following detailed description taken in conjunction with the appended claims.

DETAILED DESCRIPTION OF THE INVENTION

According to the invention, olefins (especially $C_2$-$C_6$ olefins) or higher alcohols (i.e., those containing at least 2 carbon atoms per molecule) may be efficiently produced in high yield from synthesis gas in a catalytic reaction which may comprise a single stage. In the inventive system, an alkali metal- and cobalt-containing catalyst converts synthesis gas to olefins or linear higher alcohols, preferably with ethanol as the major higher alcohol or ethylene and propylene as the major olefins.

The process of the invention is flexible in terms of its ability to be practiced at varying reaction conditions as desired, with pressure playing a major role in controlling the product composition. The composition of the feed synthesis gas can be varied widely, and generally comprises $H_2$ and CO in an $H_2$/CO molar ratio in the range of about 5:1 to about 1:5, preferably in the range of about 1:1 to about 3:1.

The reaction is generally carried out at a temperature in the range of about 450° F. to about 650° F., preferably at about 500° F. to about 560° F., and a pressure of more than about 500 psig, preferably at about 1000 to 2500 psig, if alcohols are desired, or at about 500 psig or below if olefins are desired.

At operating conditions, the effluent stream leaving the reaction zone containing the catalyst will be gaseous, but will contain condensable components (water, alcohols, etc.).

The catalyst functions to at least partially convert synthesis gas to water and saturated and unsaturated organic oxygenates having 2 or more carbon atoms per molecule. Olefins or alcohols, including higher alcohols, are also produced, and hydrocarbons which include paraffins are generally unavoidably produced as by-products.

As used herein, the term "oxygenates" includes alcohols, and the term "unsaturated oxygenates" denotes non-alcohol oxygenates such as carboxylic acids, aldehydes, ketones, and esters.

As prepared, the catalyst will generally comprise cobalt, alkali metal, zinc and possibly another metal as an inert diluent or to enhance surface area and physical strength, all in oxidized form. At operating (i.e. synthesis gas conversion) conditions, at least a portion of the oxidized cobalt will be reduced to metallic (elemental) form, but the alkali metal compound, oxidized zinc, and other metal oxide are difficulty reducible, and may persist in oxidized form during operation.

Descriptions herein of the catalyst-forming components used according to the invention are made with reference to the state of the catalyst prior to reduction under operating conditions unless otherwise specified.

The catalyst is generally characterized as a catalytically active alkali metal-containing synthesis gas conversion catalyst comprising a major weight proportion (i.e., at least about 50 wt. %) of cobalt (calculated as CoO). The catalyst is preferably substantially free of copper and other catalytically active species other than cobalt, alkali metal and, optionally, oxidized zinc, and under operating conditions preferably comprises, and highly preferably consists essentially of cobalt metal and oxidized forms of cobalt (e.g., CoO) modified by the presence of an alkali metal compound, preferably in the form of an oxide or carbonate of potassium, sodium, cesium, or rubidium. Preferred alkali metal compounds are $K_2CO_3$ and $Na_2CO_3$.

In a highly preferred form, the alkalized cobalt catalyst is further modified by the presence of oxidized zinc such as zinc oxide (ZnO) or zinc carbonate ($ZnCO_3$).

The catalyst is characterized as having a relatively low weight ratio of oxidized zinc (e.g., ZnO) to cobalt, generally in the range of zero to about 0.25, and preferably less than about 0.15, calculated as ZnO/CoO, respectively. Ratios in the range of about 0.08 to about 0.12 are preferred.

The catalyst is preferably free or substantially free of copper and other catalytically active species, including, without limitation, iron, titanium, vanadium, rhenium, catalytically active manganese, platinum, palladium, rhodium, nickel, molybdenum sulfide, chromium, tungsten, ruthenium, other catalytically active metals other than cobalt selected from Group VIII of the Periodic Table, and catalytically active metals selected from Groups IVB, V or VII of the Periodic Table. Non-catalytic metals, such as aluminum, used in some syngas conversion catalysts of the prior art are not required, although they may be present, preferably in oxide form, to enhance physical properties of the catalyst.

The term "substantially free" of copper and other catalytic species denotes that such species should not be present in amounts which materially affect the catalytic composition of the invention. More specifically, such materials, although they may be present in trace or small amounts at levels (i.e. up to about 1 wt. %, preferably less than about 0.1 wt. % of the catalyst) insufficient to affect the catalytic composition, should not be present in amounts which measurably affect the nature or level of activity of the catalyst, or which measurably change the selectivity thereof.

Stated somewhat differently, cobalt, taken in combination with the alkali metal promoter and optional oxidized zinc are substantially the only catalytically active species present in the catalyst.

Cobalt oxide-containing catalysts which are not modified with an alkali metal compound are effective in converting synthesis gas, but produce a high yield of straight chain, saturated hydrocarbons with only traces of oxygenates and olefins. Alkali metal-containing cobalt catalysts, on the other hand, are highly selective for oxygenates or olefins (depending on operating pressure). At high reaction pressures (i.e. greater than 500 psig) alkalized cobalt produces substantial yields of $C_{2+}$ ("higher") oxygenates. However, methanol is the predominant oxygenate in the product. At low reaction pressures (i.e., 500 psig and below), high yields of olefins are obtained with few oxygenated products being produced.

Since the presence of an alkali metal compound lowers the activity of cobalt-containing catalysts, relatively high reaction temperatures may be necessary or desirable with alkali metal-containing cobalt synthesis gas conversion catalysts in order to attain acceptable activities.

While the addition of an alkali metal compound to a cobalt-containing synthesis gas conversion catalyst can shift the selectivity of the catalyst from hydrocarbons to a mixture of hydrocarbons and oxygenates when operated at high pressure, incorporation of an oxidized form of zinc in addition to the alkali metal promoter can further shift the oxygenate selectivity in favor of higher oxygenates. Zinc oxide is especially preferred as a modifier for shifting the selectivity of the cobalt catalyst to higher alcohols, in particular to ethanol as the major higher oxygenate.

The product of reaction of synthesis gas over a cobalt/zinc oxide/alkali metal compound catalyst is a complex liquid mixture (at ambient conditions) consisting of two layers, with a relatively dense layer containing mostly water and low molecular weight alcohols, and a less dense layer containing other alcohols along with small amounts of acids, aldehydes, ketones, esters, and saturated hydrocarbons. Ethanol, however, is the predominant single component.

Within the general framework given above, the cobalt-containing catalyst may incorporate a variety of different modifiers and promoters. All such catalysts, however, are very active for conversion of synthesis gas, have good selectivity for higher oxygenates, especially for ethanol, and maintain good long term stability.

Additional catalyst-forming materials may include one or more catalystically inert metal oxides, such as oxides of titanium, aluminum, or manganese, preferably $TiO_2$, $Al_2O_3$, or MnO (and possibly $MnO_2$). These materials enhance the surface area and physical strength of the catalyst, and may act as a diluent to render the catalyst less active and less expensive. The additional metal oxide is preferably present in an amount of up to about 20 wt. % of the total of the cobalt (calculated as CoO) and oxidized zinc.

For example, a catalyst containing $CoO/ZnO/Al_2O_3/Na_2CO_3$ in a weight ratio of 87/9/4 (on a sodium carbonate-free basis) can withstand sulfide poisoning and still convert synthesis gas to a mixture of hydrocarbons and oxygenates. A CoO/MnO/ZnO catalyst having a weight proportion of 53/40/7 modified with potassium carbonate yields nearly 60 weight percent higher alcohols (on a water-free basis) in its a condensed liquid product when operated at high pressure in a single stage.

Cobalt should be the major catalyst component and the alkali metal and oxidized zinc components should be present in much smaller amounts in order to maintain high ethanol or ethylene selectivity compared to methanol, and high activity.

The catalyst comprises at least about 50 weight percent cobalt (calculated as CoO), up to about 10 weight percent of the alkali metal compound (calculated as the oxide), and 0 to about 20 weight percent (preferably about 5 to 15 weight percent) of oxidized zinc. The proportions of cobalt and oxidized zinc compounds are on an alkali metal-free basis, and the alkali metal compound proportion is based on the total of cobalt and zinc in the oxidized form prior to reduction at operating conditions.

Preferably, the catalyst comprises at least about 0.5 weight percent alkali metal compound (calculated as the oxide) and highly preferably 1 to 5 weight percent alkali metal compound (calculated as the oxide). The catalyst preferably comprises about 10 weight percent of oxidized zinc and about 90 weight percent cobalt (calculated as CoO), calculated on an alkali metal-free basis.

A highly preferred catalyst comprises a major weight proportion of cobalt (calculated as CoO) and is prepared by precipitating oxidized forms of cobalt with subsequent impregnation by an alkali metal compound, or coprecipitation of oxidized cobalt with an alkali metal compound.

If the cobalt oxide catalyst is to be impregnated (as opposed to coprecipitated) with an alkali metal compound, it is first precipitated as part of a non-stoichiometric complex mixture of oxidized cobalt compounds (such as oxides, hydroxides and carbonates, for example), washed, dried, and thereafter impregnated with an aqueous solution of the alkali metal compound and dried to provide a catalytic material. If desired, the dried catalytic material may be calcined prior to use in order to remove any remaining water and to convert remaining cobalt salts to oxide forms which are more readily reduced to metallic cobalt under operating conditions.

Coprecipitation can readily be effected from an aqueous solution of a soluble cobalt salt (e.g., cobalt nitrate) with addition of a soluble alkali metal compound such as sodium or potassium carbonate. The pH is then raised sufficiently to precipitate the mixture of cobalt compounds. A pH of 8-10 is typically sufficiently high to effect precipitation and may be obtained by addition of ammonium hydroxide, for example. The precipitate is washed to remove excess alkali metal and cobalt salt, dried, and optionally calcined. The precipitate must not be washed so thoroughly as to remove all alkali metal compound, of course.

If a support is desired, it is preferably added after drying of the cobalt oxide precipitate, but can be added with the soluble cobalt salt, if desired.

EXAMPLES

The following specific examples are provided in order to illustrate the practice of the invention, but are not to be construed to limit the scope of the invention. In the following examples, all percentages are expressed in terms of weight unless specified otherwise.

EXAMPLE 1

In this example, three copper-free synthesis catalysts designated A, B, and C were prepared and tested for conversion of synthesis gas under alcohol formation (i.e., high pressure) conditions. Catalyst A contained no alkali metal compound, while Catalyst B was alkalized. Catalyst C was alkalized, and additionally contained ZnO.

Catalyst preparation and testing procedures and results are set forth below.

Catalyst Preparation

Catalyst A: 194.29 g $Co(NO_3)_2 \cdot 6H_2O$ was dissolved in about 100 ml distilled water. An aqueous ammonium carbonate solution was added until the pH reached about 10. The solution was then filtered to separate the precipitate, which was washed two times with water, with filtering after each washing. The resulting solid material was dried overnight in a vacuum oven.

A portion of the uncalcined catalyst was formed into pills which were then dried in a vacuum oven for about one hour. The pills were then calcined for about one hour at 1200° F.

The resulting catalyst composition comprised substantially 100 wt.% oxidized cobalt.

Catalyst B: 194.29 g $Co(NO_3)_2 \cdot 6H_2O$ was added to 250 ml distilled water with stirring. A solution of 200 g $Na_2CO_3$ in 600 ml water was separately prepared, and added to the cobalt nitrate solution, raising the pH to about 10. The solution was filtered to separate the resulting precipitate.

The precipitate was washed twice using about 400 ml distilled water for each washing, and filtered after each washing. The catalyst was dried overnight in a vacuum oven and subsequently calcined at about 1200° F. for about two hours.

Catalyst C: 79.66 g $Co(NO_3)_2 \cdot 6H_2O$ and 7.31 g $Zn(NO_3)_2$ were added to about 150 ml distilled water with stirring. 50 g $Na_2CO_3$ was separately dissolved in about 150 ml distilled water and added to the cobalt/zinc solution, bringing the pH of the solution to about 10. The solution was filtered to separate the resulting precipitate and the precipitate was washed twice, each time in 150 ml water, filtering after each washing. The resulting material was placed in a drying oven overnight, and subsequently calcined at about 1200° F. for two hours. The resulting catalyst contained CoO, ZnO, and $Na_2CO_3$ in an approximate weight ratio of 91 wt.% CoO and 9 wt.% ZnO on a sodium carbonate-free basis.

Alcohol Synthesis Testing Procedure

Each catalyst was tested in a fixed bed continuous flow reactor for alcohol synthesis at an operating pressure of about 1500 psig using a synthesis gas comprising $H_2$ and CO in an $H_2$/CO molar ratio of about 2/1.

Catalyst A was tested at 450° F., and Catalyst B was tested at about 650° F. since the presence of an alkali metal compound lowers the activity of cobalt synthesis catalysts. The relatively high temperature was required in order to attain substantially similar activity levels for the two catalysts. Catalyst C was operated at an intermediate temperature of 540° F.

Results are summarized in Table I, below.

The selectivities of Table I are shown in a water-free basis.

TABLE I

| Catalyst | A | B | C |
|---|---|---|---|
| Conditions: | | | |
| Temp, °F. | 450 | 650 | 540 |
| Press, psig | 1500 | 1500 | 1500 |
| $H_2$/CO | 2/1 | 2/1 | 2/1 |
| % CO Conversion | 8 | 15 | 28 |
| % Selectivity | | | |
| $CO_2$ | 4 | 30 | 39 |
| Hydrocarbons | 93 | 28 | 29 |
| Methanol | 1 | 22 | 3 |
| $C_2+$ Oxygenates | 2 | 20 | 28 |

The differences in results between the tests were substantial. Unpromoted cobalt (Catalyst A) yielded more than 90wt. % straight chain, saturated hydrocarbons (as is typical of the Fisher Tropsch synthesis process), with only traces of oxygenates, whereas the alkali metal-containing Catalyst B produced 20% $C_2+$ oxygenates. Methanol was the single most predominant oxygenate in the product, and carbon dioxide and water were also products in each reaction.

While the addition of an alkali metal to unsupported cobalt shifted the selectivity from hydrocarbons to a mixture of hydrocarbons and oxygenates as shown in the foregoing comparison between Catalysts A and B, incorporation in Catalyst C of oxidized zinc (i.e. ZnO) as well as the alkali metal compound further shifted the oxygenate selectivity to $C_2+$ oxygenates, in particular to ethanol at the particular reaction conditions tested.

The product from the reaction of Catalyst C was a complex mixture consisting of two layers. The more dense layer contained mainly water and lower molecular weight alcohols, whereas the less dense layer contained alcohol along with small amounts of acids, aldehydes, ketones, esters, and saturated hydrocarbons. However, ethanol was the single most predominant component, as shown in Table II, below.

TABLE II

| ALCOHOL DISTRIBUTION OVER CATALYST C | |
|---|---|
| | Wt. % |
| Methanol | 13 |
| Ethanol | 34 |
| Propanols | 16 |
| Butanols | 19 |
| $C_5+$ Oxygenates | 18 |

EXAMPLE 2

A cobalt catalyst, designated Catalyst D, was prepared and tested for synthesis gas conversion both to higher alcohols and to olefins. The catalyst preparation and testing procedures and results are set forth below.

A solution of 168.96 g $Co(NO_3)_2 \cdot 6H_2O$ in 200 ml water was mixed with a solution of 16.45 g $Zn(NO_3)_2 \cdot 6H_2O$ in 40 ml $H_2O$ and 14.72 g $Al(NO_3)_3 \cdot 9H_2O$ in 40 ml $H_2O$.

240 g $Na_2CO_3$ was separately dissolved in 700 ml $H_2O$ and filtered before use. The resulting sodium carbonate solution was added in 50 ml increments to the cobalt-zinc-aluminum nitrate solution.

750 ml of the sodium carbonate solution was added until the final pH was about 9.6. The resulting slurry was allowed to stand overnight. Subsequently, the purple precipitate was filtered and reslurried with 750 ml $H_2O$ and refiltered. The resulting purple solid was reslurried with 750 ml $H_2O$ and again refiltered. The material was dried overnight in a vacuum oven.

The next day, the material was calcined for 1½ hour at 300° F.; ½ hour at 500° F.; ½ hour at 700° F.; ½ hour at 900° F.; and ½ hour at 1100° F.

The resulting catalyst was determined to contain $CoO/ZnO/Al_2O_3/Na_2CO_3$ in an approximate weight ratio of 87/9/4 on a sodium carbonate-free basis.

Conversion Test Procedure:

The catalyst was prereduced in 100% hydrogen at atmospheric pressure and 400° F., then lightly sulfided with 2000 ppm $H_2S$/balance $H_2$ at 250° F. for two hours.

5.0 g of Catalyst D was tested in a fixed bed continuous flow reactor at 500° F. and at two different pressures of 2000 psig and 150 psig. The feed synthesis gas contained $H_2$ and CO in an $H_2$/CO molar ratio of 1.0 and 0.9, respectively. The inlet gas flow rates at 2000 and 500 psig, respectively were 2605.5 and 2696.5 cc/hr/g.

Results are shown in Table III, below.

TABLE III

| Conditions: | | |
|---|---|---|
| Temperature. °F. | 500 | 500 |
| Pressure, psig | 2000 | 150 |
| $H_2$/CO molar ratio | 1.0 | 0.9 |
| Inlet GHSV-cc/hr/g | 2605 | 2696 |
| Product Selectivity (%) | | |
| Hydrocarbons | 22.4 | 81 |
| Oxygenates | 77.6 | ND |
| $CO_2$ | 19.1 | 18.8 |
| Hydrocarbon Selectivity (%) | | |
| $CH_4$ | 33.5 | 37.2 |
| $C_2H_6$* | 8.0 | 10.9 |
| $C_2H_4$* | 11.4 | 8.3 |
| $C_3H_8$ | 9.6 | 7.0 |
| $C_3H_6$ | 11.9 | 13.5 |
| $C_4H_{10}$ | 7.4 | 3.8 |
| $C_4H_8$ | 4.5 | 5.8 |
| $C_5H_{12}$ | 5.7 | 3.8 |
| $C_5H_{10}$ | 2.3 | 4.5 |
| $C_6+$ | 5.6 | 5.1 |
| Feed Gas Composition (vol. %) | | |
| $H_2$ | 49.5 | 47.3 |
| CO | 49.4 | 51.7 |
| $CO_2$ | 1.0 | 1.0 |

*The gas chromatographic method used in this example does not effectively separate ethylene from ethane.
ND - none detected The foregoing example demonstrates that at high pressure (2000 psig) oxygenates (including alcohols) are made in preference to hydrocarbons. At low pressure (150 psig), olefins are made in preference to paraffins with almost no production of oxygenated products.

EXAMPLE 3

In this example, two cobalt catalysts (designated E and F) were prepared and tested for activity as synthesis gas conversion catalysts.

The catalyst preparation and alcohol synthesis procedures and results are set forth below.

Catalyst Preparation

Catalyst E: 78.32 g of $Ti(OC_3H_7)_4$, titanium tetraisopropoxide, was added to 300 ml of $H_2O$ and stirred. To this mixture was added 230.04 g of $Co(NO_3)_2 \cdot 6H_2O$, 26.28 g $Zn(NO_3)_2 \cdot 6H_2O$, and 4.24 g $K_2CO_3$. The resulting mixture was stirred for approximately one hour. A separately prepared 6M $Na_2CO_3$ solution in water was slowly added until the pH was approximately 10. The resulting solid precipitate was filtered and washed twice, each time with 300 ml $H_2O$. The washed solid was then dried overnight at 250° C. in a vacuum oven. The resulting catalyst was then calcined for two hours at 1200° F. The nominal composition of this catalyst was 67.9% CoO, 20.6% $TiO_2$, 8.2% ZnO, and 3.3% $K_2O$ on a carbonate-free basis. About 5% to 10% residual sodium carbonate remained in the catalyst.

Catalyst F: 318.6 g $Co(NO_3)_2 \cdot 6H_2O$ and 29.2 g $Zn(NO_3)_2 \cdot 6H_2O$ were dissolved in 600 ml $H_2O$. Separately, 200 g $Na_2CO_3$ was dissolved in 600 ml $H_2O$. The $Na_2CO_3$ solution was slowly added to the cobalt solution until the pH was approximately 10. The resulting solid precipitate was filtered and washed twice, each time with 500 ml $H_2O$. The washed solid was dried overnight at 250° F. in a vacuum oven and calcined for two hours at 1200° F. The nominal composition of the catalyst was 91% CoO and 9% ZnO on a carbonate-free basis. Approximately 5% to 10% residual $Na_2CO_3$ remained in the catalyst.

Testing Procedure

The catalysts were tested for alcohol synthesis in a fixed-bed, continuous-flow pilot plant. Yields were determined by gas chromatography. The flow rate was controlled by mass flow controllers and metered from the test unit by a wet test meter. The gas flow rate (cc of gas per gram of catalyst per hour) and carbon monoxide analysis were determined prior to reaction and again at the reaction temperature. The liquid products were collected for about 24 hours and analyzed by gas chromatography. Liquid samples were tested for water content (percent) by Karl Fischer analysis.

Catalyst E: 5.0 g of Catalyst E was diluted with an equal volume of high surface area carbon and loaded into a fixed-bed reactor. The reaction pressure was 1500 psig. The inlet feed gas composition was 44.5 vol. % CO, 7.7 vol. % $CO_2$, and 47.8 vol. % $H_2$. The total gas flow rate was 2392 cc/hr/g catalyst. The reaction temperatures were 575° F. and 590° F., as indicated in Table IV. The catalyst was tested for several days at these conditions. The results of the test are summarized in Table IV.

The product contained low yields of methanol and high yields of $C_{2+}$ alcohols. Many other oxygenated products were also present. Additionally, the liquid product consisted of two layers, one a predominately organic (alcohol) layer and one a predominately water layer. Both layers contained significant levels of both water and alcohols. The water content in the total liquid product was approximately 45 wt. %.

Catalyst F: 5.0 g of Catalyst F was diluted with an equal volume of high surface area carbon and loaded into a fixed-bed reactor. The reaction pressure was 1500 psig. The inlet feed gas composition was 46.9 vol. % CO, 8.3 vol. % $CO_2$, and 44.8 vol. % $H_2$. The total gas flow rate was 2399 cc/hr/g catalyst. The reaction temperature was 540° F.

Again the product contained relatively little methanol with high levels of $C_{2+}$ alcohols and other $C_{2+}$ oxygenates. The product also separated into two layers, an aqueous layer and an oxygenate layer. The total liquid product was analyzed to contain approximately 40 wt. % water. Catalyst results are summarized in Table IV.

TABLE IV

| Catalyst: | E | | F |
|---|---|---|---|
| Catalyst Components: | CoO—$TiO_2$—ZnO—$K_2O$ | | CoO—ZnO |
| Temperature, °F. | 575 | 590 | 540 |

TABLE IV-continued

| Catalyst:<br>Catalyst Components: | E<br>CoO—TiO$_2$—ZnO—K$_2$O | | F<br>CoO—ZnO |
|---|---|---|---|
| Pressure, psig | 1500 | 1500 | 1500 |
| CO Conversion, % | 14.2 | 13.3 | 16.5 |
| Selectivity: | | | |
| (%) CO$_2$ | 44.4 | 42.1 | 41.4 |
| CH$_4$ | 10.5 | 10.1 | 12.2 |
| C$_{2+}$ Hydrocarbons | 18.7 | 19.7 | 16.6 |
| MeOH | 0.9 | 2.6 | 1.4 |
| C$_{2+}$ Alcohols | 7.7 | 11.7 | 14.5 |
| Other | 18.0 | 13.8 | 14.0 |
| Yields (g/hr/g catalyst) | | | |
| CH$_4$ | .011 | .010 | .016 |
| C$_{2+}$ Hydrocarbons | .018 | .017 | .019 |
| MeOH | .0018 | .0049 | .0037 |
| C$_{2+}$ Alcohols | .010 | .014 | .024 |
| % C$_{2+}$ Alcohols in Organic Phase of Liquid | 28.9 | 41.1 | 48.4 |
| % Water in Total Liquid | 45% | 45% | 40% |

EXAMPLE 4

In this example, a cobalt catalyst (designated G) was prepared and tested for synthesis gas conversion activity.

The catalyst preparation and testing procedures and results are set forth below.

Catalyst Preparation—Catalyst G 19.58 g of Ti(OC$_3$H$_7$)$_4$, titanium tetraisopropoxide, was added to 300 ml of H$_2$O and stirred. To this mixture was added 57.51 g of Co (NO$_3$)$_2$·6H$_2$O, 6.57 g Zn(NO$_3$)$_2$·6H$_2$O and 1.06 g K$_2$CO$_3$. The resulting mixture was stirred for approximately one hour. A separately prepared 6M Na$_2$CO$_3$ solution in water was slowly added until the pH was approximately 10. The resulting solid precipitate was filtered and washed twice, each time with 300 ml H$_2$O. The washed solid was then dried overnight at 250° C. in a vacuum oven. The resulting catalyst was then calcined for two hours at 1200° F. The nominal composition of this catalyst was 67.9% CoO, 20.6% TiO$_2$, 8.2% ZnO and 3.3% K$_2$O on an Na$_2$CO$_3$-free basis. About 5% to 10% residual sodium carbonate retained in the catalyst.

Testing Procedure

Catalyst G was tested for alcohol synthesis in a fixed bed, continuous flow pilot plant using the procedure of Example 1, above.

5.0 g of Catalyst G was loaded into a fixed bed reactor and tested at a pressure of 200 psig, and at temperatures of 550° F. and 600° F. The synthesis gas feed was 46.4 vol. % CO, 8.3 vol. % CO$_2$, and 45.3 vol. % H$_2$. The inlet gas flow rate was 2401 cc/hr/g catalyst. Additionally, the catalyst was tested at 1500 psig and a temperature of 570° F. The results are summarized in Table V, below.

TABLE V

| Catalyst:<br>Catalyst Components: | G<br>CoO—TiO$_2$—ZnO—K$_2$O | | |
|---|---|---|---|
| Temperature, °F. | 550 | 600 | 570 |
| Pressure, psig | 200 | 200 | 1500 |
| Product Selectivity, % (CO$_2$-free basis) | | | |
| MeOH | ND | ND | 7.9 |
| C$_{2+}$ oxygenates* | ND | ND | 77.9 |
| CH$_4$ | 41.0 | 58.9 | 6.1 |
| C$_{2+}$ hydrocarbons | 59.0 | 41.1 | 8.4 |
| % C$_{2+}$ oxygenates* (in liquid) | ND | ND | 91.2 |
| Hydrocarbon Selectivity, % (CO$_2$-free basis) | | | |
| CH$_4$ | 41.0 | 58.9 | |
| C$_2$H$_6$ | 3.1 | 7.2 | |
| C$_2$H$_4$ | 19.7 | 7.5 | |
| C$_3$H$_8$ | 2.3 | 2.3 | |
| C$_3$H$_6$ | 20.7 | 8.3 | |
| C$_4$H$_{10}$ | — | 0.5 | |
| C$_4$H$_8$ | 2.9 | 1.9 | |
| C$_5$H$_{12}$ | — | 1.6 | |
| C$_5$H$_{10}$ | 1.5 | 1.0 | |
| C$_{6+}$ | 9.0 | 10.0 | |
| Olefin/Paraffin Ratio | | | |
| C$_2$ | 6.4 | 1.1 | |
| C$_3$ | 9.1 | 3.6 | |
| C$_4$ | >10 | 3.5 | |
| C$_5$ | >10 | 0.6 | |

*Includes many unidentified compounds, assumed to be oxygenates.
ND = none detected These results indicate that when the catalyst is operated at high reaction pressures the predominant products are oxygenates, especially C$_{2+}$ oxygenates; while, at low reaction pressures the same catalyst yields hydrocarbons, especially C$_2$ to C$_6$ olefins, as the predominant products.

EXAMPLE 5

In this example, a cobalt catalyst (designated H) was prepared and tested for activity as a synthesis gas conversion catalyst.

The catalyst preparation and alcohol synthesis procedures and results are set forth below.

Catalyst Preparation—Catalyst H

Solutions of 398.3 g of Co(NO$_3$)$_2$·6H$_2$O in 350 ml H$_2$O, and 36.5 g Zn(NO$_3$)$_2$·6H$_2$O in 50 ml distilled H$_2$O were separately prepared. The two solutions were added to a beaker and stirred. A solution of 250 g Na$_2$CO$_3$ in 900 ml distilled H$_2$O was slowly added to the cobalt-zinc solution and stirred for about 1 hour, and filtered with #3 filter paper.

The filter cake was reslurried twice, each time with 1000 ml H$_2$O, and filtered.

The resulting catalyst was dried in a vacuum oven overnight and then placed in a dessicator.

The resulting catalyst was then calcined, and the pore volume was determined to be 0.31 ml H$_2$O/g catalyst.

The catalyst comprised CoO and ZnO in approximate 91/9 weight proportion, and Na$_2$CO$_3$.

Testing Procedure

Catalyst H was tested for alcohol synthesis in a fixed bed, continuous flow pilot plant using the procedure of Example 1, above.

5.0 g of Catalyst H was loaded into a fixed bed reactor, and tested at a pressure of 1580 psig, and a temperature of 540° F. The synthesis gas feed was 30.7 vol. % CO, 5.4 vol. % CO$_2$, and 63.9 vol. % H$_2$. The inlet gas flow rate was 2447.0 cc/hr/g catalyst. Results are summarized in Table VI, below.

TABLE VI

| Catalyst:<br>Catalyst Components: | H<br>CoO—ZnO—Na$_2$CO$_3$ |
|---|---|
| Temperature, °F. | 540 |

TABLE VI-continued

| Catalyst: | H |
|---|---|
| Catalyst Components: | CoO—ZnO—Na$_2$CO$_3$ |
| Pressure, psig | 1580 |
| CO Conversion, % | 30.5 |
| Selectivity: | |
| (%) CO$_2$ | 38.9 |
| CH$_4$ | 12.9 |
| C$_2$+ Hydrocarbons | 15.9 |
| MeOH | 2.6 |
| C$_2$+ Alcohols | 17.8 |
| Other | 11.8 |
| Yields (g/hr/g catalyst) | |
| CH$_4$ | 0.021 |
| C$_2$+ Hydrocarbons | 0.023 |
| MeOH | 0.009 |
| C$_2$+ Alcohols | 0.06 |
| % C$_2$+ Alcohols in Organic Phase of Liquid | 55 |
| C$_2$+ Olefins/C$_2$+ paraffins | 0.91 |

The foregoing detailed description is given for clearness of understanding only, and no unnecessary limitations should be understood therefrom, as modifications within the scope of the invention will be apparent to those skilled in the art.

We claim:

1. A process for converting synthesis gas comprising a mixture of H$_2$ and carbon monoxide, said process comprising the step of contacting synthesis gas with a synthesis gas conversion catalyst under synthesis gas conversion conditions including a pressure of 500 psig or below or more than 500 psig whereby said synthesis gas is converted to olefins or alcohols having at least 2 carbon atoms per molecule, respectively, said catalyst consisting essentially of catalytically active species of at least about 50 wt. % cobalt (calculated as CoO), 0 to about 20 wt. % oxidized zinc, and about 0.5 to about 10 wt. % said alkali metal compound (calculated as oxide), the weight ratio of said oxidized zinc to said cobalt being in the range of about 0 to about 0.25, said cobalt and oxidized zinc proportions being calculated on an alkali metal-free basis and said alkali metal compound proportion being based on the total of said oxidized zinc and said cobalt prior to reduction under said conversion conditions.

2. The process of claim 1 wherein said oxidized zinc is a compound selected from the group consisting of ZnO and ZnCO$_3$.

3. The process of claim 2 wherein said oxidized zinc comprises between about 5 wt. % and 15 wt. of the total of said cobalt and said oxidized zinc.

4. The process of claim 1 wherein said catalyst comprises oxidized cobalt, metallic cobalt and said alkali metal compound under said conversion conditions.

5. The process of claim 4 wherein said alkali metal compound is selected from the group consisting of oxides, hydroxides, and carbonates of an alkali metal selected from the group consisting of potassium, sodium, cesium, and rubidium.

6. The process of claim 5 wherein said alkali metal compound is selected from the group consisting of oxides and carbonates of potassium and sodium.

7. The process of claim 4 wherein said catalyst is prepared by a method comprising the steps of precipitating said oxidized cobalt as part of a non-stoichiometric complex mixture containing one or more of the group consisting of cobalt oxides, hydroxides, and carbonates, washing and drying the resulting precipitate, thereafter impregnating said precipitate with a solution of said alkali metal compound, and drying said impregnated precipitate to provide a catalytic material.

8. The process of claim 4 wherein said catalyst is prepared by a method comprising the step of co-precipitating said oxidized cobalt with said alkali metal compound, followed by washing and drying the resulting precipitate to provide a catalytic material.

9. The process of claim 1 wherein said catalyst is supported on a material selected from the group consisting of diatomaceous earth, porous carbon, and silica.

10. The process of claim 1 wherein said contacting step is carried out at a temperature in the range of about 450° F. to about 650° F.

11. The process of claim 10 wherein said contacting step is carried out at a temperature of about 500° F. to about 560° F.

12. The process of claim 1 wherein said contacting steps is carried out at a pressure of about 500 psig or less.

13. The process of claim 14 wherein said pressure is between about 200 psig and about 500 psig.

14. The process of claim 1 wherein said process is carried out at a pressure of more than about 500 psig.

15. The process of claim 14 wherein said pressure is about 1000 psig to about 2500 psig.

16. A process for converting synthesis gas comprising a mixture of H$_2$ and carbon monoxide, said process comprising the step of contacting synthesis gas with a synthesis gas conversion catalyst under synthesis gas conversion conditions including a pressure of 500 psig or below or more than 500 psig whereby said synthesis gas is converted to olefins or alcohols having at least 2 carbon atoms per molecule, respectively, said catalyst under operating conditions consisting essentially of catalytically active species of at least about 50 wt. % cobalt as oxidized and metallic cobalt, about 5 wt. % to about 15 wt. % of an oxidized zinc compound, and about 0.5% to about 10 wt. % of an alkali metal compound selected from the group consisting of oxides, hydroxides, and carbonates of an element selected from the group consisting of potassium, sodium, cesium, and rubidium, the weight ratio of said oxidized zinc compound to said cobalt being in the range of about 0 to about 0.25, said cobalt and zinc proportions being calculated on an alkali metal-free basis, and said alkali metal compound proportion being based on the total of said oxidized zinc compound and cobalt prior to reduction under said conversion conditions.

17. The process of claim 16 wherein said oxidized zinc compound is selected from the group consisting of ZnO and ZnCO$_3$.

18. The process of claim 16 wherein said alkali metal compound is selected from the group consisting of oxides and carbonates of potassium and sodium.

19. The process of claim 16 wherein said catalyst is prepared by a method comprising the steps of precipitating said oxidized cobalt as part of a non-stoichiometric complex mixture containing one or more of the group consisting of cobalt oxides, hydroxides, and carbonates, washing and drying the resulting precipitate, thereafter impregnating said precipitate with a solution of said alkali metal compound, and drying said impregnated precipitate to provide a catalytic material.

20. The process of claim 16 wherein said catalyst is prepared by a method comprising the step of co-precipitating said oxidized cobalt with said alkali metal compound, followed by washing and drying the resulting precipitate to provide a catalytic material.

21. A process for converting synthesis gas comprising a mixture of $H_2$ and carbon monoxide, said process comprising the step of contacting synthesis gas with a synthesis gas conversion catalyst under synthesis gas conversion conditions including a pressure of 500 psig or below or more than 500 psig whereby said synthesis gas is converted to olefins or alcohols having at least 2 carbon atoms per molecule, respectively, said catalyst under operating conditions consisting essentially of catalytically active species of at least about 50 wt. % cobalt (calculated as CoO) as oxidized and metallic cobalt, about 5 wt. % to about 15 wt. % of an oxidized zinc compound selected from the group consisting of ZnO and $ZnCO_3$, and about 0.5 wt. % to about 10 wt. % of an alkali metal compound (calculated as oxide) selected from the group consisting of oxides and carbonates of potassium and sodium, the weight ratio of said oxidized zinc compound to said cobalt being in the range of about 0 to about 0.25, said cobalt and zinc compound proportions being calculated on an alkali metal-free basis, and said alkali metal compound proportion being based on the total of said oxidized zinc compound and cobalt prior to reduction under said conversion conditions.

22. The process of claim 21 wherein said catalyst is prepared by a method comprising the steps of precipitating said oxidized cobalt as part of a non-stoichiometric complex mixture containing one or more of the group consisting of cobalt oxides, hydroxides, and carbonates, washing and drying the resulting precipitate, thereafter impregnating said precipitate with a solution of said alkali metal compound, and drying said impregnated precipitate to provide a catalytic material.

23. The process of claim 21 wherein said catalyst is prepared by a method comprising the step of co-precipitating said oxidized cobalt with said alkali metal compound, followed by washing and drying the resulting precipitate to provide a catalytic material.

24. A process for converting synthesis gas comprising a mixture of $H_2$ and carbon monoxide to alcohols having at least 2 carbon atoms per molecule, said process comprising the step of contacting synthesis gas with a synthesis gas conversion catalyst under synthesis gas conversion conditions including a pressure of more than about 500 psig whereby said synthesis gas is converted to alcohols having at least 2 carbon atoms per molecule, said catalyst consisting essentially of catalytically active species of at least about 50 wt. % cobalt (calculated as CoO), 0 to about 20 wt. % oxidized zinc, and about 0.5 to about 10 wt. % of an alkali metal compound (calculated as oxide), the weight ratio of said oxidized zinc to said cobalt being in the range of about 0 to about 0.25, said cobalt and oxidized zinc proportions being calculated on an alkali metal-free basis and said alkali metal compound proportion being based on the total of said oxidized zinc and said cobalt prior to reduction under said conversion conditions.

25. The process of claim 24 wherein said oxidized zinc comprises between about 5 wt. % and 15 wt. % of the total of said cobalt and said oxidized zinc.

26. The process of claim 24 wherein said catalyst comprises oxidized cobalt, metallic cobalt and said alkali metal compound under said conversion conditions.

27. The process of claim 24 wherein said contacting step is carried out at a temperature in the range of about 450° F. to about 650° F.

28. The process of claim 27 wherein said contacting step is carried out at a temperature of about 500° F. to about 560° F.

29. The process of claim 24 wherein said pressure is about 1000 psig to about 2500 psig.

* * * * *